(12) United States Patent
Tetzner et al.

(10) Patent No.: US 7,723,026 B2
(45) Date of Patent: May 25, 2010

(54) METHOD FOR INVESTIGATING CYTOSINE METHYLATION IN DNA BY MEANS OF DNA REPAIR ENZYMES

(75) Inventors: Reimo Tetzner, Berlin (DE); Kurt Berlin, Stahnsdorf (DE); Jürgen Distler, Berlin (DE)

(73) Assignee: Epigenomics AG, Berlin (DE)

( * ) Notice: Subject to any disclaimer, the term of this patent is extended or adjusted under 35 U.S.C. 154(b) by 453 days.

(21) Appl. No.: 10/585,682

(22) PCT Filed: Jan. 10, 2005

(86) PCT No.: PCT/EP2005/000231

§ 371 (c)(1),
(2), (4) Date: Jan. 25, 2007

(87) PCT Pub. No.: WO2005/068648

PCT Pub. Date: Jul. 28, 2005

(65) Prior Publication Data

US 2007/0160995 A1    Jul. 12, 2007

(30) Foreign Application Priority Data

Jan. 9, 2004    (DE) .................. 10 2004 002 257

(51) Int. Cl.
*C12Q 1/68* (2006.01)
*C12P 19/34* (2006.01)

(52) U.S. Cl. .......................... 435/6; 435/91.2
(58) Field of Classification Search ............ None
See application file for complete search history.

(56) References Cited

U.S. PATENT DOCUMENTS 5,656,430 A    8/1997    Chirikjian et al.
6,265,171 B1 *  7/2001   Herman et al. .............. 435/6
6,340,566 B1 *  1/2002   McCutchen-Maloney ...... 435/6

FOREIGN PATENT DOCUMENTS

| AU | 200018565 | * | 6/2000 |
| DE | 19853398 C1 | | 3/2000 |
| DE | 10204566 A1 | | 8/2003 |

OTHER PUBLICATIONS

Gitan et al., "Methylation-Specific Oligonucleotide Microarray: A New Potential for High-Throughput Methylation Analysis," Genome Research, 2002, vol. 12, No. 1, pp. 158-164.*
Kavli et al., J. Biol. Chem., 277(42):39926-36 (Oct. 18, 2002).
Bazar et al., "Mutation identification DNA analysis system (MIDAS) for detection of known mutations," Electrophoresis, 20:1141-8 (1999).
Zhang et al., "An amplification and Ligation-Based Method to Scan for Unknown Mutations in DNA," Human Mutation, 20:139-47 (2002).

* cited by examiner

*Primary Examiner*—Kenneth R. Horlick
(74) *Attorney, Agent, or Firm*—Kriegsman & Kriegsman

(57) ABSTRACT

The following invention concerns a method for investigating cytosine methylation by means of DNA repair enzymes. Here, the DNA is first converted so that unmethylated cytosines are converted to uracil, while 5-methylcytosine remains unchanged. Then the DNA is hybridized to oligonucleotides, whereby hybrids will be formed with or without erroneous base pairings, in each case depending on the methylation status of the DNA. Following this, the erroneously paired hybrids will be cleaved by repair enzymes. Then the methylation status of the DNA can be determined in different ways. The method according to the invention is particularly suitable for the diagnosis and prognosis of cancer disorders and other diseases associated with a change of the methylation status as well as for predicting undesired drug effects.

14 Claims, No Drawings

METHOD FOR INVESTIGATING CYTOSINE METHYLATION IN DNA BY MEANS OF DNA REPAIR ENZYMES

BACKGROUND OF THE INVENTION

The present invention concerns a method for the detection of 5-methylcytosine in DNA. 5-Methylcytosine is the most frequent covalently modified base in the DNA of eukaryotic cells. It plays an important biological role, among other things, in the regulation of transcription, in genetic imprinting and in tumorigenesis (for review: Millar et al.: Five not four: History and significance of the fifth base. In: The Epigenome, S. Beck and A. Olek (eds.), Wiley-VCH Publishers, Weinheim 2003, pp. 3-20). The identification of 5-methylcytosine as a component of genetic information is thus of considerable interest. The detection of methylation is difficult, since cytosine and 5-methylcytosine have the same base pairing behavior. Many of the conventional detection methods based on hybridization thus cannot distinguish between cytosine and methylcytosine. In addition, the methylation information is completely lost in a PCR amplification.

The conventional methods for methylation analysis operate essentially according to two different principles. In the first, methylation-specific restriction enzymes are used, and in the second, a selective chemical conversion of unmethylated cytosines to uracil occurs (e.g. by means of bisulfite treatment, see, e.g.: DE 101 54 317 A1; DE 100 29 915 A1). The DNA that has been pretreated enzymatically or chemically is then amplified and can be analyzed in different ways (for review: WO 02/072880 pp. 1 ff). Methods which can detect methylation in a sensitive and quantitative manner are of great interest. This is true due to the important role of cytosine methylation in the development of cancer, particularly with respect to diagnostic applications. Of particular importance are methods which permit detection of deviant methylation patterns in body fluids, e.g., in serum. Unlike unstable RNA, DNA is often encountered in body fluids. The DNA concentration in blood is in fact increased in destructive pathological processes such as cancer disorders. The diagnosis of cancer by means of a methylation analysis of tumor DNA found in body fluids is thus possible and has in fact been described many times (see e.g.: Palmisano et al.: Predicting lung cancer by detecting aberrant promoter methylation in sputum. Cancer Res. 2000 Nov. 1; 60(21):5954-8). A particular problem however, consists of the fact that in body fluids, in addition to the DNA with the methylation pattern typical of disease there is also a large quantity of DNA of identical sequence but of another methylation pattern to be found. The diagnostic methods must thus be able to detect small quantities of particularly methylated DNA against an intense background of DNA of the same sequence but of another methylation pattern (hereinafter also referred to as 'background DNA').

The conventional methods for methylation analysis solve this problem only to a limited extent. Usually the chemically pretreated DNA is amplified by means of a PCR method. A selective amplification of only methylated (or in the opposite approach, of only unmethylated) DNA is assured by the use of methylation-specific primers or blockers. The use of methylation-specific primers is known as a "methylation-sensitive PCR" ("MSP"; Herman et al.: Methylation-specific PCR: a novel PCR assay for methylation status of CpG islands. Proc Natl Acad Sci USA. 1996 Sep. 3; 93(18):9821-6). A comparably sensitive method is the so-called "HeavyMethyl" method. Here, a specific amplification of only the originally methylated (or unmethylated) DNA is obtained by use of methylation-specific blocker oligomers (for review: WO 02/072880). Both MSP and the "HeavyMethyl" method can be applied as quantifiable real-time variants. These make possible the detection of the methylation status of a few positions directly in the course of the PCR without the need for a subsequent analysis of the products ("MethyLight"—WO 00/70090; U.S. Pat. No. 6,331,393). One such embodiment is the "Taqman" method. This technique uses probe molecules which bear a fluorescent-dye/quencher pair. The probes hybridize in a sequence-specific manner to the amplificates and are decomposed in the course of the next amplification cycle by the exonuclease activity of the polymerase. A detectable fluorescent signal arises due to the separation of quencher and dye (see, e.g., Eads et al.: MethyLight: a high-throughput assay to measure DNA methylation. Nucleic Acids Res. 2000 Apr. 15; 28(8):E32).

Another MethyLight embodiment is the so-called Lightcycler method. In this case, two different probes are utilized, which hybridize to the amplificate in the direct vicinity of one another, and then produce a detectable signal via fluorescence-resonance energy transfer (FRET).

The applicability of this method for a sensitive and specific detection of methylated DNA against a large background of unmethylated DNA is of course limited. The danger exists that false-positive results will occur by means of a nonspecific amplification of background DNA. In order to increase the specificity of the amplification, it is thus necessary to use primers or blocker sequences, in which several methylation-specific positions are contained. These sequence requirements, in turn, limit the applicability of the method.

Based on the particular biological and medical importance of cytosine methylation and due to the above-mentioned disadvantages of the prior art, there is a great technical need for the development of high-performance methods for methylation analysis. Such a method is described in the following.

According to the invention, the DNA to be investigated is first chemically pretreated, after which it is hybridized to oligonucleotide probes and then reacted with DNA repair enzymes. One embodiment of the invention permits a specific decomposition of background DNA. A selective amplification of only the DNA whose methylation status will be detected, is thereby facilitated. A very sensitive and very specific analysis of methylation is thus enabled. The field of application of the method according to the invention is thus broader than that of the methodologies already known (see above). Methylation-specific primer or blocker sequences are not necessary to the same extent.

Another embodiment of the method according to the invention utilizes hybridization and the application of DNA repair enzymes, not for the decomposition of background DNA, but directly for the detection of the methylation status. A similar method for mutation analysis is described under the name "Midas" (Bazar et al.: Mutation identification DNA analysis system (MIDAS) for detection of known mutations. Electrophoresis. 1999 June; 20(6):1141-8; U.S. Pat. No. 5,656,430). In this case, an oligonucleotide is hybridized to the DNA to be investigated. An erroneous base pairing is formed at the mutation to be detected, which is then recognized by a mismatch repair enzyme. The probe is cleaved at this site, and the fragments can be detected by different methods. If an excess of probe is used, then the process can be reiterated. Another similar method for mutation analysis has been described by Zhang et al. (An amplification and ligation-based method to scan for unknown mutations in DNA. Hum Mutat. 2002 August; 20(2):139-47). Here, the DNA to be investigated is first amplified by means of a PCR. Then the amplificates are cross-hybridized with the formation of erroneous base pairings. After this, breaks in the single strand are introduced by reaction with repair enzymes. Finally, primers are ligated specifically to the cleaved DNA, by means of which the mutation can be specifically detected.

The application of these two methods to methylation analysis is described for the first time below. Based on the particular biological and medical importance of cytosine methylation and due to the disadvantages of the known methods, the discovery of this advantageous new technology represents an important technical advance.

All patents, patent applications and publications referred to or cited herein, or from which a claim for benefit of priority has been made, are incorporated by reference in their entirety to the extent they are not inconsistent with the explicit teachings of this specification.

DESCRIPTION

As used herein the term 'erroneously paired hybrids' shall be taken to mean a nucleic acid double strand comprising one or more base pair mismatches.

As used herein the term 'hybrid' shall refer to a double stranded DNA consisting of at least one oligonucleotide hybridized to a treated genomic DNA.

The term 'target sequence' shall refer to a polynucleotide sequence to which an oligonucleotide hybridizes to.

The term 'mismatch' shall refer to any base pairing excluding the pairs Adenine and Thymine; Adenine and Uracil; Cytosine and Guanine. Particularly preferred according to the present invention are the following base pair mismatches: Guanine and Thymine; Guanine and Uracil; Cytosine and Adenine.

As used herein the term 'AP' position shall be taken to mean apurinic or apyrimidinic. As used herein the term 'background DNA' shall be used to define DNA relative to a DNA of interest and wherein the determination of the methylation status of said DNA of interest may be an object of further or simultaneous investigation. Said background DNA shall be taken to mean a DNA sequence of a specific methylation status wherein said DNA sequence has the identical sequence but different methylation status to a DNA of interest.

The method according to the invention uses DNA repair enzymes for the analysis of cytosine methylation. The invention is thus based on the following principle: First, the DNA to be investigated is converted such that originally methylated and unmethylated DNA can be distinguished from each other by their base sequence. Then the DNA to be investigated is hybridized to oligonucleotides. The base sequence of said oligonucleotides is complementary to a target sequence within said DNA to be investigated wherein the CpG methylation status of said target sequence is of a specified methylation status (i.e. methylated or unmethylated prior to treatment). In one embodiment, the hybridization is carried out under conditions of stringency such that the oligonucleotides are capable of hybridizing to said target sequence within said DNA to be investigated wherein the CpG methylation status (prior to treatment) of said target sequence is NOT of said specified methylation status. Accordingly said oligonucleotides may hybridise to a non-complementary target sequence such that base pair mismatches (hereinafter also referred to as erroneous pairings) are formed at positions at which differential methylation was present. Thereby either hybrids with erroneous pairings or hybrids without erroneous pairings will be formed, depending on the methylation status of the DNA. In another embodiment the oligonucleotide sequence and the stringency conditions are selected such that either hybrids with erroneous pairings or no hybrids will be formed, depending on the methylation status of the DNA. The erroneously paired hybrids are recognized by DNA repair enzymes and cleaved.

In one embodiment a hydrolytic cleavage of both strands (oligo and polynucleotide) is performed.

Then the methylation state of the DNA can be determined in different ways.

Accordingly, the method according to the invention involves a method for the analysis of cytosine methylation, which is characterized in that a) the DNA to be investigated is chemically or enzymatically converted so that 5-methylcytosine remains unchanged, while unmethylated cytosine is converted to uracil or to another base which differs from cytosine in its base pairing behavior, b) the converted DNA is hybridized to oligonucleotides, whereby the DNA of one methylation status forms hybrids with erroneous base pairings, while the DNA of the other methylation status forms hybrids without erroneous base pairings or does not form hybrids, c) one strand of the erroneously paired hybrids is enzymatically cleaved, d) the uncleaved DNA or the cleaved fragments are detected, e) the methylation status of the investigated DNA is concluded from the detection signal generated in step d).

The method according to the invention can be conducted by means of two embodiments. In the first variant, erroneous base pairings are formed at precisely those positions whose methylation status will be investigated. Accordingly, either hybrids with erroneous base pairings or without erroneous base pairings will form during hybridization. In the second variant, the erroneous base pairings are not formed at the positions to be investigated, but at other base pair positions. Hybrids with erroneous base pairings or no hybrids form, in each case depending on the methylation status of the DNA.

The first embodiment is characterized in that in step b) above, the DNA of one methylation status forms hybrids with erroneous base pairings, while the DNA of the other methylation status forms hybrids without erroneous base pairings.

The second embodiment is characterized in that in step b) above, the DNA of one methylation status forms hybrids with erroneous base pairings, while the DNA of the other methylation status forms no hybrids at all.

In the first step of both embodiments, the DNA to be investigated is reacted with a chemical or with an enzyme such that 5-methylcytosine remains unchanged, while unmethylated cytosine is converted to uracil or to another base which differs from cytosine in its base pairing behavior. The DNA to be investigated can thus originate from different sources depending on the diagnostic or scientific objective. For diagnostic objectives, tissue samples are preferably used as the initial material, but body fluids, particularly serum, can also be used. It is especially preferred to use body fluid samples, when the method being subject of the invention is used as a diagnostic tool for an 'early screening'. In this situation a body fluid sample will be the only sample available.

Therefore in one embodiment of the present invention, the method of the invention is further characterized in that the sample DNA is obtained from body fluids of an individual. 'Body fluid' herein refers to a mixture of macromolecules obtained from an organism. This includes, but is not limited to, blood, blood plasma, blood serum, urine, sputum, ejaculate, semen, tears, sweat, saliva, lymph fluid, bronchial lavage, pleural effusion, peritoneal fluid, meningal fluid, amniotic fluid, glandular fluid, fine needle aspirates, nipple aspirate fluid, spinal fluid, conjunctival fluid, vaginal fluid, duodenal juice, pancreatic juice, bile and cerebrospinal fluid. This also includes experimentally separated fractions of all of the preceding. 'Body fluid' also includes solutions or mixtures containing homogenised solid material, such as faeces.

It is also preferred that the sample DNA is obtained from tissue sources, such as for example provided as clinical samples, for example tissue embedded in paraffin, histological slides or fresh frozen tissue. These tissues may be for example, tissue from eyes, intestine, kidneys, brain, heart, prostate, lungs, breast or liver, or all possible combinations thereof.

It is especially preferred to use DNA from serum, plasma, sputum, stool, urine, sperm or cerebrospinal fluid. Preferably, the DNA is first isolated from the biological specimen. The DNA is extracted according to standard methods, e.g., from blood with the use of the Qiagen UltraSens DNA extraction kit. The isolated DNA may then be fragmented, e.g., by reaction with restriction enzymes. The reaction conditions and the enzymes employed are known to the person skilled in the art and are taken e.g., from the protocols supplied by the manufacturers. Then the DNA is chemically or enzymatically converted. Chemical conversion by means of bisulfite is preferred. Several variants of the bisulfite conversion are known to the person skilled in the art (see e.g. Frommer et al.: A genomic sequencing protocol that yields a positive display of 5-methylcytosine residues in individual DNA strands. Proc Natl Acad Sci USA. 1992 Mar. 1; 89 (5):1827-31; Olek, A modified and improved method for bisulphite based cytosine methylation analysis. Nucleic Acids Res. 1996 Dec. 15; 24(24):5064-6.; DE 100 29 915; DE 100 29 915 [sic]). The bisulfite conversion is most preferably conducted in the presence of denaturing solvents, e.g., dioxane, and a radical scavenger (see DE 100 29 915). In another preferred embodiment, the DNA is not chemically converted, but rather enzymatically converted. This is conceivable e.g., by use of cytidine deaminases wherein unmethylated cytidines react more rapidly than methylated cytidines. A corresponding enzyme has been recently identified (Bransteitter et al.: Activation-induced cytidine deaminase deaminates deoxycytidine on single-stranded DNA but requires the action of RNase. Proc Natl Acad Sci USA. 2003 Apr. 1; 100(7):4102-7).

Methylated and unmethylated DNA are converted into different DNA sequences by the chemical or enzymatic pretreatment. Thus the sequences differ only at those positions that prior to treatment were differentially methylated. For example, after bisulfite treatment, a cytosine is present at an originally methylated cytosine position, while a uracil is present at an originally unmethylated cytosine position. Otherwise, both DNA sequences are identical. The invention takes advantage of this by subsequent hybridization of oligonucleotides to the target region of the converted DNA polynucleotides. In one embodiment, the oligonucleotides are completely complementary to only one of the converted sequences. The other sequence forms erroneous base pairings with the oligonucleotides at the differently methylated positions.

As naturally occurring DNA is double stranded and the treatment as described above changes the hybridization properties of these strands the treatment results in two strands which do not form hybrids anymore. Their sequences differ. However, both strands generated that way can be taken to be analysed, as the methylation information is still contained in both strands, the "sense" strand as well as the "antisense" strand.

In the second step of the method according to the invention, the converted DNA is hybridized to oligonucleotides, whereby in one embodiment hybrids will be formed with or without erroneous base pairings, and in the other embodiment hybrids with erroneous base pairings will be formed or no hybrids will be formed, in each case depending on the methylation status of the DNA.

The second embodiment, may be performed in two variants: In the first variant, erroneous base pairings are formed at precisely those positions whose methylation status will be investigated. In the second variant, the erroneous base pairings are not formed at the positions to be investigated, but at other base pair positions. Hybrids with erroneous base pairings or no hybrids form, in each case depending on the methylation status of the DNA.

In the case of bisulfite-treated DNA, only a limited type of erroneous base pairing will be considered. The originally unmethylated DNA contains a uracil at the sites where a cytosine is found in the methylated strand. Correspondingly, depending on the sequence of the oligonucleotide utilized, U<->G or C<->A erroneous pairings occur. If the DNA to be investigated is first amplified after the bisulfite treatment, then additional erroneous pairings can be utilized. Instead of uracil, thymine nucleoside triphosphates are provided in the course of the amplification and then a T<->G erroneous pairing is also made available. In addition, after an amplification, for the first time, the newly created complementary strands (copies of the first converted strand) are also investigated (due to the bisulfite conversion, at first only two DNA strands are formed, which are no longer complementary to one another). It is thus also possible to utilize A<->C or G<->T erroneous pairings. It is obvious that additional erroneous pairings can occur, if the oligonucleotides contain other than the conventional DNA bases. If the probes bear a uracil, for example, instead of thymine, G<->U erroneous pairings can also occur. Corresponding embodiments are included in this application.

Which of the above-named erroneous pairings are used according to the invention for the detection of methylation depends on the investigation objective, on the further experimental procedure and on the enzymes utilized. The same holds true for the question of whether the utilized oligonucleotides form erroneously paired hybrids with the DNA to be detected (i.e. the DNA of interest) or with the background DNA. The method according to the invention can be adapted in different embodiments.

In one embodiment of the invention, the DNA whose methylation status (methylated or unmethylated) is to be detected forms hybrids comprising mismatched base pairs (hereinafter also referred to as erroneously paired hybrids). In the following steps, the oligonucleotide component of these hybrids is then enzymatically cleaved. The oligonucleotide fragments are isolated from the DNA and then detected. The methylation status of the DNA can be concluded from the signal. With excess oligonucleotides, the process can be repeated. The signal can thus be amplified (Midas method, see further details below).

In another embodiment of the method according to the invention, the background DNA forms erroneously paired hybrids. The DNA, whose methylation status is to be detected, in contrast, forms hybrids without erroneous pairing. The background DNA strand of the erroneously paired hybrid is then specifically cleaved by means of an enzyme (in contrast, the above-described embodiment is different in that the oligonucleotide component of the erroneously paired hybrids is cleaved therein). Finally, the intact DNA (which did hybridize without erroneous base pairings) is detected.

Which erroneous base pairings are utilized in this embodiment also depends on the specificity of the enzymes used in the next step (see below).

In the third step of the method according to the invention, one strand of the erroneously paired hybrids is enzymatically cleaved. This may be either the oligonucleotide or the converted DNA strand. The enzymes utilized must be able to recognize the above-described erroneous pairings and cleave the hybrids at these sites. DNA repair enzymes are particularly suitable for this purpose. Particularly preferred for the use according to the invention are DNA glycosylases, which cleave the glycosidic bond between the base and the sugar-phosphate backbone. Also preferred are DNA glycosylases which simultaneously possess an apurine/apyrimdine (AP) lyase activity, which results in the cleavage of the DNA backbone (for review: Memisoglu and Samson: Base excision repair in yeast and mammals. Mutat Res. 2000 Jun. 30; 451 (1-2):39-51). Also preferred is the use of the TDG protein (Thymine-DNA glycosylase). Said protein comprises a Thymine-DNA glycosylase, which recognizes T<->G erroneous pairings and cleaves only the strand with the T. The use of heat-stable variants of the TDG protein are also a preferred embodiment (Horst and Fritz: Counteracting the mutagenic effect of hydrolytic deamination of DNA 5-methylcytosine residues at high temperature: DNA mismatch N-glycosylase Mig. Myth of the thermophilic archaeon *Methanobacterium thermoautotrophicum* EMBO J. 1996 Oct. 1; 15(19):5459-69). The use of MutY DNA glycosylase is also particularly preferred for the method according to the invention. This enzyme specifically recognizes A<->G erroneous pairings and cleaves only the A strand (see: Lu and Hsu: Detection of single DNA base mutations with mismatch repair enzymes. Genomics. 1992 October; 14(2):249-55). Another particularly preferred enzyme is the Mug protein. This specifically recognizes U<->G erroneous pairings (see: Lutsenko and Bhagwat: The role of the *Escherichia coli* mug protein in the removal of uracil and 3, N(4)-ethenocytosine from DNA. J Biol Chem. 1999 Oct. 22; 274(43):31034-8). All three named enzymes are commercially available (Trevigen Inc., 8405 Helgerman Court, Gaithersburg, Md. 20877 USA; www.trevigen.com). A plurality of other repair enzymes are known in the art and suitable for use in the method of the invention (see, e.g.: Wood et al.: Human DNA repair genes. Science. 2001 Feb. 16; 291(5507):1284-9;). It is known to the person skilled in the art that repair enzymes which cannot cleave the sugar-phosphate backbone can also be used in combination with lyases or endonucleases (see: Bazar et al., loc. cit. 1999; U.S. Pat. No. 5,656,430, column 5 Z 23 ff). Furthermore, it is also known that AP positions can be cleaved physically or by reaction with chemicals, e.g., with NaOH (see: Horst and Fritz, loc. cit., 1996). It is an alternative embodiment of the method to utilize the AP positions without further treatment, if the enzymatically treated DNA is later amplified. It is to be expected that an amplification of the abasic DNA can only be carried out to a limited extent. The method according to the invention also includes embodiments in which both strands of the erroneously paired hybrids are cleaved.

In the fourth step of the method according to the invention, either the uncleaved DNA or the cleaved fragments are detected by means of a detectable signal. Said detection may be by any means known in the art, preferred is the use of detectable labels incorporated in to said oligonucleotides. Any suitable labels known in the art may be used including but not limited to fluorescence labels, radionuclides, or detachable molecule fragments having a typical mass that can be detected in a mass spectrometer. Where said labels are mass labels, it is preferred that the labeled amplificates have a single positive or negative net charge, allowing for better detectability in the mass spectrometer. The detection may be carried out and visualized by means of, e.g., matrix assisted laser desorption/ionization mass spectrometry (MALDI) or using electron spray mass spectrometry (ESI). Wherein said label is a fluorescent label it is particularly preferred that said oligonucleotide is labeled with a FRET pair such that one label is present upstream of the AP site and the other label is present downstream of said site. Degradation of the oligonucleotide results in spatial separation of the two dyes which is indicated by the resulting increase in fluorescence.

Different embodiments are possible depending on the previous experimental structure. In the hereinafter referred to as 'Midas' variant of the method according to the invention, the cleaved oligonucleotide fragments are detected. Any suitable means known in the art may be used for said detection, including but not limited to gel or capillary electrophoresis or by observation of the detectable labels, in particular fluorescence labels, radionuclides, or detachable molecule fragments.

In embodiments in which repair enzymes are utilized in order to remove the background DNA, the intact DNA (i.e. the DNA of interest) can be analyzed by means of any suitable molecular biology techniques, e.g., by hybridization or sequencing. The converted DNA is preferably amplified prior to said analysis by means of a polymerase reaction (see below), including but not limited to PCR. It is particularly preferred that the use of repair enzymes described above is performed is simultaneously with said amplification. This is possible, e.g., with the use of heat-stable enzymes (see below). The intact DNA is then detected. This may be carried out by any means known in the art including hybridization-based methods such as, but not limited to, array technology and probe based technologies as well as by means of techniques such as sequencing and template directed extension.

In the fifth step of the method according to the invention, the methylation status of the investigated DNA is concluded from the detection signal generated either by detection of cleaved fragments in the above described first embodiment or in the second embodiment by detection of the unfragmented converted DNA.

Particular embodiments of the method according to the invention are described in the following.

In a first particularly preferred embodiment, the method according to the invention is characterized in that the following steps are conducted:

a) the DNA to be investigated is chemically or enzymatically converted so that 5-methylcytosine remains unchanged, while unmethylated cytosine is converted to uracil or to another base which differs from cytosine in its base pairing behavior, b) the converted DNA is hybridized to oligonucleotides, whereby the DNA to be detected (which is the DNA of interest) forms hybrids with erroneous base pairings, c) the oligonucleotide strand of the erroneously paired hybrids is enzymatically cleaved, d) the cleaved oligonucleotide fragments are detected, e) the methylation status of the investigated DNA is concluded from the signal.

Optionally before step d) the cleaved oligo fragments may be isolated from the hybridizing strand, for example by applying denaturing conditions.

In this embodiment of the method according to the invention, the DNA to be investigated is first pretreated chemically or enzymatically to convert the nucleic acids as described above. It is particularly preferred that said treatment is by means of bisulfite treatment. Procedures and reaction conditions are known to the person skilled in the art (see: Frommer et al., loc. cit. 1992; Olek et al., loc. cit., 1996; DE 100 29915; DE 100 29915 [sic]). The treated DNA may then optionally but preferably be amplified. The converted DNA is then hybridized to oligonucleotides, whereby the DNA to be detected (methylated or unmethylated) forms erroneously paired hybrids. In the following steps, the oligonucleotide component of these hybrids is enzymatically cleaved, wherein said cleavage is dependent on the presence or absence of base pair mismatches. The oligonucleotide fragments are then separated from the DNA and detected. The methylation status of the DNA can then be concluded from the detected fragments. In a further preferred embodiment of the method excess oligonucleotides are present and the process is repeated. The signal can thus be amplified.

The reaction components and reaction conditions are similar to those described known in the art. The oligonucleotide probes are preferably between 20 and 50 nucleotides long. The oligonucleotide probes are preferably labeled by means of dyes or other detectable labels, which facilitate detection. The erroneous pairings and the enzymes must be selected in such a way that only the oligonucleotide components of the hybrids are cleaved. Care must be taken so that during the treatment (most preferably bisulfite conversion), unmethylated Cytosine is converted to Uracil, while methylcytosine remains unchanged. Accordingly, preferred erroneous base pairs in this embodiment are Uracil mismatched with Guanine and Thymine mismatched with Guanine (wherein the CG position of interest is unmethylated prior to treatment) and Cytosine mismatched with Adenine (wherein the CG position of interest is methylated prior to treatment). Correspondingly, the oligonucleotides utilized must comprise a G or an A at the respective position. The enzymes employed cleave either a G at a U<->G erroneous pairing or an A at a C<->A erroneous pairing. If the DNA to be investigated is first amplified after the bisulfite treatment, then T<->G, A<->C or G<->T erroneous pairings can also be utilized (see above). The oligonucleotides thus comprise at least one G, C or T. The cleavage of a G<->T erroneous pairing at T is possible, e.g. due to the use of the commercially available TDG enzyme (see above).

The oligonucleotide probes are hybridized to the DNA preferably under stringent conditions. It is preferred that said stringency should be such that only the mismatches are able to occur at the CpG positions to be analysed within the target sequence. The degree of such stringency will thus be variable and dependent on multiple factors. Nucleic acid duplex or hybrid stability is expressed as the melting temperature or Tm, which is the temperature at which a probe dissociates from a target DNA. This melting temperature is used to define the required stringency conditions. The establishment of suitable hybridization conditions is known to one skilled in the art.

For example it is useful to first establish the lowest temperature at which only homologous hybridization occurs with particular reaction conditions. Then, assuming that 1% mismatching results in a 1° C. decrease in the Tm, the temperature of the final hybridization reaction is reduced accordingly (for example, if sequences having >95% identity with the probe are sought, the final wash temperature is decreased by 5° C.). In practice, the change in Tm can be between 0.5° C. and 1.5° C. per 1% mismatch.

The reaction parameters are preferably selected so that the bond of the probe to the DNA is thermodynamically unstable after the enzymatic cleavage, so that the cleaved fragments fall away from the DNA. These target sequences can then repeatedly be hybridized to oligonucleotides that have not been enzymatically digested. Embodiments are also possible, in which a fragment of the probe remains bound to the DNA and is extended, e.g., with labeled oligonucleotides (see: U.S. Pat. No. 5,656,430). In a further embodiment of the method helix-destabilizing molecules may be used to further facilitate displacement of the oligonucleotide from the target sequence. In a further embodiment of the method heat-stable repair enzymes may be used in order to increase the sensitivity of the method. (Bazar et al., loc. cit. 1999; U.S. Pat. No. 5,656,430).

In the last step of this embodiment, the cleaved oligonucleotide fragments are detected. Any means standard in the art may be used including but not limited to gel or capillary electrophoresis or via fluorescence-resonance energy transfer.

Another particularly preferred embodiment of the method according to the invention utilizes the formation of erroneously paired hybrids in particular for removing background DNA. The invention thereby facilitates the detection of DNA of interest (hereinafter also referred to as DNA to be detected).

The following embodiment is characterized in that a) the DNA to be investigated is chemically or enzymatically converted so that 5-methylcytosine remains unchanged, while unmethylated cytosine is converted to uracil or to another base which differs from cytosine in its base pairing behavior, b) the converted DNA is hybridized to oligonucleotides, whereby the background DNA forms hybrids with erroneous base pairings, c) the DNA strand of the erroneously paired hybrids is enzymatically cleaved, d) the intact (i.e. uncleaved) DNA is detected, e) the methylation status of the investigated DNA is concluded from the detection signal generated in step d).

In this embodiment the DNA sample is also first pretreated enzymatically or chemically. Preferably a bisulfite conversion is conducted (see above). The oligonucleotides are then hybridized to the pretreated DNA sample, such that the DNA to be detected hybridises to the target sequence without the formation of any mismatches and wherein the background DNA forms erroneously paired hybrids. Said mismatches are subsequently specifically cleaved by means of an enzyme. The uncleaved, i.e. the intact DNA is then preferably amplified. The amplificates are detected and the methylation status of the DNA is concluded from detection of the uncleaved DNA and/or amplificate thereof.

The oligonucleotides are preferably between 10 and 100, and most preferably between 20 and 50 nucleotides in length. In particular embodiments of the invention, the oligonucleotides serve simultaneously as primers or probes in a subsequent amplification (see below). If the oligonucleotides are not to be further utilized as primers, they are preferably constructed in such a way that they cannot be extended by a polymerase utilized in the amplification. This is performed, e.g., by using 3'-deoxy-oligonucleotides or oligonucleotides functionalized differently at the 3'-position, for example 3'-O-acetyl-oligonucleotides. In addition, the oligonucleotides are preferably constructed in such a way that they will not be degraded by the polymerase during the amplification. This can be accomplished, e.g., by thioate bridges at the 5'-end. Another possibility is to use polymerases which do not have a nuclease activity. In a preferred embodiment of the invention, the oligonucleotide, serves as a so-called Taqman probe. In such an embodiment it is required that the polymerase has an exonuclease activity in order to assure decomposition of the probe (see below).

The oligonucleotides are preferably utilized in concentrations from 0.1 μmol/l to 10 μmol/l. The concentrations of the remaining components are preferably selected in such a way that they are suitable for the subsequent amplification (e.g.: 50-100 mmol/L KCl, 10 mmol/l Tris; 1.5-5 mmol/l $Mg^{2+}$, pH 8.5-9.0). Otherwise, the hybridization conditions are selected such that a specific hybridization occurs with the formation of the desired erroneous pairings. Particulars for determining hybridization conditions are known to the person skilled in the art. The use of oligonucleotides which have a so-called "minor groove" binder (ABI) may also be used. The specific binding of short oligonucleotides is thus possible.

In a preferred embodiment, the oligonucleotides include several methylation-specific positions, so that several erroneous base pairings occur in the formation of hybrids with the background DNA. In this way, the probability that the background DNA is cleaved is increased.

Preferably, the oligonucleotides include 3, most preferably they comprise 4-5 methylation specific positions. It is most preferred that these methylation specific positions are CpG dinucleotides Preferably, the repair enzymes utilized only cleave the pretreated DNA strand of the hybrid (i.e. the polynucleotide, instead of the oligonucleotide). Nevertheless, this invention also includes embodiments, in which both hybrid strands are cleaved. Possible erroneous base pairings, as described above, including U<->G and C<->A are preferred, as also preferred are T<->G, A<->C or G<->T following amplification. The enzymes utilized must be able to recognize these erroneous pairings and cleave the DNA component at these sites. In a preferred embodiment, the TDG enzyme is utilized, which cleaves T<->G erroneous pairings at the T position (see above). In another preferred embodiment, the Mug protein is utilized, which cleaves the U<->G erroneous pairings at the U position.

In a preferred embodiment of the method according to the invention, the hybridization is conducted and the repair enzymes are employed prior to the DNA amplification. This method is particularly suitable if heat-stable variants of the repair enzymes are not available. The reaction conditions are to be selected in such a way that it is assured that the background DNA will be degraded as completely as possible. Details are known to the person skilled in the art and are taken, e.g., from the protocols supplied by commercial suppliers of such enzymes.

In another particularly preferred embodiment, the use of repair enzymes is conducted simultaneously with the amplification. It is preferred that heat-stable enzymes are used in this embodiment (see below). Heat-stable variants of the TDG enzyme are known and are commercially available (Horst and Fritz, loc. cit., 1996, Trevigen Inc., 8405 Helgerman Court, Gaithersburg, Md. 20877 USA; www.trevigen.com). Such a parallel procedure saves time and facilitates automation. In addition, as background DNA that may be amplified non-specifically is removed from the amplification process the danger of false-positive results is reduced. When there is simply a pre-incubation with the repair enzymes it is conceivable that the enzymatic degradation does not run to completion. Insufficiently degraded background DNA may then be amplified and thus lead to false-positive results.

In further optional steps of the method the DNA of interest (i.e. intact DNA) is detected. Intact DNA is preferably detected by means of an amplification. If an incomplete degradation of the background DNA cannot be excluded, then the amplification and/or the detection of the DNA is preferably carried out in a methylation-specific manner, i.e., with the use of methylation-specific primers, blockers or probes. The specificity of the detection of DNA of interest is thus further increased, and the danger of false-positive results is further reduced. Methylation-specific amplification and detection are part of the prior art (MSP, HeavyMethyl, Methyl-Light detections (see above).

In another preferred embodiment, the oligonucleotides and the primers of the subsequent (methylation-specific) amplification are identical. These variants are similar to the known MSP method (see above). The specificity and range of application, however, are higher than in the case of the MSP method. It has often been necessary previously, for diagnostic applications of the MSP method, to utilize primers with at least three methylation-specific positions. It must only be assured that there is no nonspecific extension of the erroneously paired primers and thus no false-positive signals. These sequence requirements and the necessity of a co-methylation of the investigated positions limit the applicability of the method. In the variants according to the invention, a nonspecific extension of erroneously paired primers is prevented by the use of repair enzymes. The erroneously paired positions are then specifically degraded by the repair enzymes. If the sugar-phosphate backbone is cleaved at the position of erroneous pairing, then the background DNA is no longer available for an amplification. Therefore for a methylation-specific amplification only a small number of methylation-specific positions are necessary.

For this embodiment, a pre-incubation is preferably conducted with the repair enzyme. If the reaction mixture already contains the DNA polymerase for the subsequent amplification, then it must be assured that a nonspecific extension of the erroneously paired primers does not occur during the pre-incubation. This can be done, e.g., with the use of a "hot start" polymerase, which is activated only by a heating step (see: Birch et al., "Simplified hot start PCR", Nature. 1996 May 30; 381(6581):445-6).

In addition to a pre-incubation, it is a further embodiment of the invention to employ the repair enzyme and to conduct the amplification in parallel (i.e. simultaneously). A nonspecific amplification of the erroneously paired primers, however, must also be excluded here. This is achieved, for example, if polymerases are available whose activity begins only starting from an elevated temperature. An additional step must also be integrated into the PCR temperature profile. An annealing of the primer to the DNA with the formation of erroneous pairings is then made possible first at a low temperature during the course of the temperature cycle. At this temperature, the repair enzyme degrades the background DNA; the polymerase of course is still inactive. The temperature is then increased. The erroneously paired primers are separated from the DNA, and the polymerase extends the specifically bound primers.

In another preferred embodiment, the oligonucleotides are constructed in such a way that they can serve simultaneously as detection probes in the subsequent amplification. Probe formats, which enable the real-time detection, are preferably used, e.g. Taqman, Lightcycler or Molecular Beacon probes. In order to prevent false-positive signals, it must be assured that the formation of erroneously paired hybrids and the methylation-specific detection of the probes take place at different times from one another. This particularly applies when a Taqman probe is employed, in which the signal is formed via the decomposition of the probe by means of the polymerase. It must be assured here that the polymerase does not become active too early during the use of the repair enzyme. This can be achieved by employing a pre-incubation with the use of a "hot-start" polymerase (see above). When employing a Taqman probe, it is possible to conduct the degradation of erroneous pairings and the amplification in parallel only if polymerases are available which become active starting from an elevated temperature (see above). When Lightcycler and Molecular Beacon probes are employed in contrast it is sufficient if operation is conducted with multistep temperature profiles during the amplification. In this way, the annealing of the probes to the DNA with the formation of erroneous pairings is first produced at a low temperature. The repair enzyme degrades the background DNA at this temperature, and the temperature is then increased And the erroneously paired probes are then separated from the DNA. Amplification of the DNA is conducted along with a detection of the specifically bound probes.

The invention encompasses all combinations of the above-named embodiments. In particular the embodiments concerning methylation-specific primers and probes which serve simultaneously as erroneous pairing probes are preferred.

Another preferred embodiment of the invention is to amplify several fragments simultaneously by means of a multiplex PCR. In its design, care must be taken that not only the primers, but also the additionally utilized oligonucleotides must not be complementary to one another, as this complicates high-degree multiplexing. In the case of chemically or enzymatically pre-treated DNA however, one has the advantage that a forward primer can never function as a reverse primer, due to the different G and C content of the two DNA strands, which in turn facilitates the multiplexing and essentially compensates for the above-described disadvantage. The amplificates can be detected by means of any methods known in the art. In this way, e.g., the use of real-time variants is encompassed. For the amplification of more than four genes, it is preferred to detect the amplificates using methods other than real-time detection, in such cases DNA hybridization arrays are preferred (see below).

In another particularly preferred embodiment, the repair enzymes are utilized in a microarray-based methylation analysis. The microarray-based methylation analysis is known in the art (see: Adorjan et al.: Tumour class prediction and discovery by microarray-based DNA methylation analysis. Nucleic Acids Res. 2002 Mar. 1; 30(5):e21). Here, the DNA to be investigated is first bisulfite treated and amplified by means of a PCR. Subsequently the amplificates are hybridized to oligonucleotides, which are immobilized on a surface. Two different types of oligonucleotides are utilized: oligonucleotides which comprise CG dinucleotides (detection of the methylated status) and oligonucleotides which comprise TG dinucleotides (detection of the unmethylated status). One problem in chip analysis is that it may produce false results due to nonspecific hybridizations. According to the invention, during hybridization repair enzymes are utilized which directly remove the erroneously paired DNA. The specificity of the chip-based methylation analysis can thus be increased.

The above-described embodiments are characterized in that the erroneous base pairings occur precisely at positions whose methylation status is to be investigated. Accordingly, either hybrids with erroneous base pairings or without erroneous base pairings will form during hybridization. In a further embodiment, the erroneous base pairings are formed outside the positions to be investigated. Depending on the methylation status of the DNA each time, either hybrids with erroneous base pairings form or no hybrids form.

This second embodiment for the analysis of cytosine methylation is accordingly characterized in that a) the DNA to be investigated is chemically or enzymatically converted so that 5-methylcytosine remains unchanged, while unmethylated cytosine is converted to uracil or to another base which differs from cytosine in its base pairing behavior, b) the converted DNA is hybridized to oligonucleotides, whereby the DNA of one methylation status forms hybrids with erroneous base pairings, while the DNA of the other methylation status does not form hybrids, c) one strand of the erroneously paired hybrids is enzymatically cleaved, d) the intact DNA or the cleaved fragments are detected, e) the methylation status of the investigated DNA is concluded the detected intact DNA or cleaved fragments.

The DNA to be investigated is first enzymatically or chemically converted as described above. In order to achieve a methylation-specific hybridization, the oligonucleotides utilized must comprise methylation-specific dinucleotides (CG, TG or CA). These oligonucleotides then bind specifically to either methylated or to unmethylated DNA. In addition, outside of the positions to be investigated, the oligonucleotides comprise a base which results in erroneous pairing in the hybridization with the DNA to be analyzed. The hybridization conditions are thus selected so that a hybrid formation occurs only with the DNA of one methylation status. This hybrid then comprises an erroneous pairing. The DNA of the other methylation state, in contrast, does not form hybrids under the selected hybridization conditions. In order to assure such a specific hybridization, oligonucleotides are preferably utilized, which bear at least 3, preferably 4-6 methylation-specific dinucleotides. The oligonucleotides are thus preferably between 20-40 nucleotides long. Hybridization conditions which tolerate the formation of one erroneous pairing, but do not permit the formation of other erroneous pairings at the methylation-specific positions belong to the prior art. The person skilled in the art can easily determine these via computer programs or via standard tests. This embodiment has the advantage in comparison to the above-described variants that random erroneous pairings can be introduced into the hybrids. A limitation to the preferred mismatches U<->G, C<->A, T<->G, A<->C or G<->T (see above) no longer exists. The number of usable enzymes thus also increases. Information on usable repair enzymes is available to the person skilled in the art, e.g., in Wood et al. (loc. cit. 2001). In principle, it is also possible to use oligonucleotides that bear chemically modified bases, which are recognized by the repair enzymes. It is thus within the scope of the invention that the modified bases in the hybrids do not form erroneous pairings, and the recognition by repair enzymes proceeds only on the basis of the chemical modification. Such a variant has the advantage that a hybridization can take place under very specific conditions. For embodiments in which the DNA components of the hybrids are cleaved enzymes must be available which cleave the DNA strand.

In addition, these two basic embodiments can be conducted in different variants. In one variant, the oligonucleotides form hybrids with the DNA whose methylation status is to be detected. The oligonucleotide components of the hybrids are cleaved and the fragments are detected (see above). In another variant, the oligonucleotides bind only to the background DNA. Then the background DNA is subsequently cleaved by the repair enzymes. Preferably the DNA to be detected is then amplified and finally detected. It is preferred that the repair enzymes are employed prior to the amplification of the DNA. This method is particularly suitable if heat-stable variants of the repair enzymes are not available. The reaction conditions are to be selected in such a way that it is assured that the background DNA is degraded as completely as possible (see above). If heat-stable repair enzymes are available, then it is preferred to perform the repair enzymes step and to the amplification step simultaneously (see above).

In a particularly preferred variant of this embodiment, a methylation-specific amplification is conducted by means of blocker oligonucleotides (the so-called "HeavyMethyl" method, see above), wherein the utilized oligonucleotides that form erroneous pairings are thus identical to the blocker oligonucleotides. Thus a nonspecific amplification of the background DNA leading to false-positive results is prevented in two ways. Methods for the synthesis of blocker oligonucleotides and for conducting the "HeavyMethyl" method are known to the person skilled in the art (see: WO 02/072880).

Another aspect of the invention consists of the use of all embodiments according to the invention. If disease-specific cytosine positions are investigated, then the method according to the invention is particularly suitable for the diagnosis or prognosis of cancer disorders or other diseases associated with a change of methylation status. These include, among others, CNS malfunctions; symptoms of aggression or behavioral disturbances; clinical, psychological and social consequences of brain damage; psychotic disturbances and personality disorders; dementia and/or associated syndromes; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as a consequence of an abnormality in the development process; malfunction, damage or disease of the skin, the muscles, the connective tissue or the bones; endocrine and metabolic malfunction, damage or disease; headaches or sexual malfunction. The method according to the invention is also suitable for predicting undesired drug effects, for establishing a specific drug therapy (personalized medicine) and for monitoring the success of a drug therapy. Another application is distinguishing cell types or tissues and investigating cell differentiation.

It is especially preferred to apply the method that is subject of the invention in the clinical field of early screening or early diagnosis. Here the aim is to test individuals before they suffer severe symptoms and therefore usually no biopsy material (tissue derived) is available, but body fluid samples may be used. Therefore it is especially preferred that the method according to the invention is employed for the early diagnosis of a cancer disorders or other diseases associated with a change in the cytosine methylation status. It is furthermore preferred that the nucleic acids to be investigated has been taken from (i.e. isolated from or derived from) a body fluid sample of an individual. The sample types serum, plasma, sperm, urine or stool are especially preferred.

Finally the subject of the present invention is also a kit, comprising at least one oligonucleotide probe, and a repair enzyme as well as optionally a polymerase and additional reagents necessary for a PCR.

The preferred embodiment is a kit, comprising a repair enzyme, at least one oligonucleotide probe, characterized as hybridizing to nucleic acids, which have been converted according to step a of the method being subject of the invention, and by containing a mismatching base position. It is preferred that said kit comprises a polymerase and additional reagents necessary for a PCR.

EXAMPLES

Example 1

Methylation-Specific Amplification After a Specific Decomposition of Unmethylated Template DNA by Means of the *E. coli* Mug Protein A sequence of the brca1 gene of the human genome (Seq ID-8, nt 3538 to nt 3666 in Genebank Accession L78833.1) is amplified by means of PCR. Bisufite-converted human DNA which was obtained from peripheral blood and was universally methylated by means of Sss1 methylase (Serologicals) serves as the template. Human DNA also obtained from peripheral blood was used as unmethylated background DNA (Roche Diagnostics). It is known from this that the sequence of the brca1 gene to be amplified is present unmethylated. Thus a mixture of methylated and unmethylated bisulfite-converted DNA can be produced. The bisulfite conversion was conducted as described in Olek et al. (loc. cit). In this chemical reaction, all cytosine bases are converted to uracil bases, while 5-methylcytosine is not converted. Due to the identical base pairing properties of uracil and thymine, those positions, which correspond to the converted, unmethylated cytosine, are designated with a lower-case "t" (or a lower-case "a" in the complementary strand). In contrast, the capital "T" (or "A" in the complementary strand) stands for the thymine that is already present prior to the bisulfite treatment. The primers used in this example are specific for bisulfite-converted DNA. However, they do not contain methylation-specific sequences. A methylation-dependent reaction is obtained only with the use of a mismatch probe, which is recognized by the Mug protein. For this purpose, an oligonucleotide which is sequence-specific for the brca1 gene is added to the reaction batch. This oligonucleotide hybridizes to the fragment to be amplified and thus spans two CpG dinucleotides. The sequence of the mismatch probe is selected such that at 37° C. it binds both to the methylated bisulfite-converted DNA as well as also to the unmethylated bisulfite-converted DNA. The hybridization to unmethylated bisulfite-converted DNA is thus produced with the formation of two U<->G erroneous base pairings. A 30-minute incubation at 37° C. in which the U<->G erroneous pairing is recognized by the *E. coli* Mug protein takes place prior to the PCR. The Mug protein then removes the uracils from the DNA (Lutsenko et al., 1999, loc. cit.). Therefore, two abasic nucleotides are formed in the unmethylated DNA. In contrast, the methylated bisulfite-converted DNA remains unchanged. This produces no erroneous base pairing with the hybridization probe and thus does not represent a substrate for the Mug protein. In a 10-minute activation step for the DNA polymerase at 95° C., the abasic regions of the formerly unmethylated DNA are partially cleaved hydrolytically. The use of the mismatch probe and the Mug protein thus leads to a specific decomposition of unmethylated DNA. It should be noted here that the hydrolytic cleavage does not run to completion under the selected conditions. Nevertheless, the unmethylated DNA is no longer available as the template for the PCR, since the abasic region which is produced cannot be read by the polymerase. Therefore, PCR products can only be produced from a DNA sample if it contains a certain fraction of DNA which is present methylated in the region of the mismatch probe. The reaction batch is passed into capillaries provided for it in the LightCycler-1.3 system.

The following are contained in 20 µl of reaction volume (sequences in Table 2): 10 µl of template DNA (Table 1), 2 µl of Faststart LightCycler Mix for hybridization probes (Roche Diagnostics), 2.0 mmol/l $MgCl_2$ (Roche Diagnostics), 0.30 µmol/l forward primer (Seq ID-1, TIB-MolBiol, Berlin), 0.30 µmol/l reverse primer (Seq ID-2, TIB-MolBiol), 0.15 µmol/l probe 1 (Seq ID-3, TIB-MolBiol), 0.15 µmol/l probe 2 (Seq ID-4, TIB-MolBiol), 1 unit of Mug protein (Trevigen), 1 µmol/l mismatch probe (Seq ID-5, TIB-MolBiol).

The following temperature program is utilized: Pre-incubation with Mug protein: 40 min at 37° C.; activation of the polymerase: 10 min at 95° C.; 55 temperature cycles: 10 sec at 95° C.; 10 sec at 56° C.; 10 sec at 72° C. Then the reaction is cooled to 35° C.

The fluorescent signals are measured in channel F2. The evaluation of the PCR is conducted automatically by means of the LightCycler software in channel F2/F1. Signals which lie significantly above the background signal of the negative controls are considered positive. It is expected as a result that only those DNA mixtures which contain methylated bisulfite-converted DNA produce positive signals. The signals should be independent of the quantity of original unmethylated background DNA. The results that are expected are shown in Table 1.

Example 2

Methylation-Specific PCR with the Use of the Heat-Stable TDG Protein from *Methanobacterium thermoautotrophicum* THF The same DNA sequence as described in Example 1 is amplified by means of PCR. The bisulfite-converted human DNA also described therein is used as the template DNA. In this application example, a heat-stable thymine DNA glycosylase from *Methanobacterium thermoautotrophicum* THF (TDG protein) is added to the PCR batch (Horst et al., 1996, loc. cit.) This recognizes T<->G erroneous pairings and removes thymine from the DNA double strand. The guanine bases are still obtained. A sequence-specific oligonucleotide is also found in the reaction batch (mismatch probe). The sequence of the mismatch probe in this case is selected such that it is complementary to the methylated bisulfite-converted DNA and spans at least one CpG. During the annealing phase of the PCR, the mismatch probe binds to the template DNA. The hybridization to formerly unmethylated template DNA and the amplification produced therefrom occur with the formation of T<->G erroneous base pairings. These are recognized by the TDG protein and the thymine is removed from the DNA, so that abasic regions are formed. This DNA with abasic regions is then no longer available as a template in the next PCR cycle, since it cannot be read by the DNA polymerase. The denaturing phases of the PCR serve simultaneously for the partially hydrolytic cleavage of the DNA at the abasic nucleotides. This cleaved DNA also can no longer serve as the template. Since the TDG protein is heat-stable, it remains active over prolonged periods of time and can catalyze the specific degradation of formerly unmethylated DNA strands over several PCR cycles. Originally methylated DNA, in contrast, is not degraded, since it forms regular C:G pairings with the mismatch probe. Formerly methylated DNA and corresponding amplificates become enriched over the duration of the PCR. Therefore, only sequences of methylated DNA are expected as the end product of the PCR. Consequently, PCR products can only be produced from a DNA sample if it contains a certain fraction of DNA which is present methylated in the region of the mismatch probe. The advantage of this method in contrast to Application Example 1 lies in the fact that the selection between originally methylated and unmethylated DNA occurs not only once, but in several PCR cycles. By the use of heat-stable TDG protein from *Methanobacterium thermoautotrophicum* THF, a higher relative sensitivity of the reaction is thus achieved. The temperature program contains two additional incubation cycles at 56° C., in order to reduce the fraction of unmethylated DNA even prior to the beginning of the PCR. The reaction batch is passed into capillaries provided for it in the LightCycler-1.3 system.

The following are contained in 20 µl of reaction volume (sequences in Table 2): 10 µl of template DNA, 2 µl of FastStart Lightcycler Mix for hybridization probes (Roche Diagnostics), 2.0 mmol/l $MgCl_2$ (Roche Diagnostics), 0.30 µmol/l forward primer (Seq ID-1, TIB-MolBiol), 0.30 µmol/l reverse primer (Seq ID-2, TIB-MolBiol); 0.15 µmol/l probe 1 (Seq ID-3, TIB-MolBiol); 0.15 µmol/l probe 2 (Seq ID-4, TIB-MolBiol), 1 unit of heat-stable TDG glycosylase (Trevigen), 1 µmol/l mismatch probe (Seq ID-6, TIB-MolBiol).

The following temperature program is utilized: 2 temperature cycles: 10 sec at 95° C.; 5 min at 56° C.; activation of the polymerase: 10 min at 95° C.; 55 temperature cycles: 10 sec at 95° C.; 10 sec at 56° C.; 10 sec at 72° C. Then the reaction is cooled to 35° C.

The fluorescent signals are measured in channel F2. The evaluation of the PCR is conducted automatically by means of the LightCycler software in mode F2/F1. Signals which lie significantly above the background signal of the negative controls are considered positive. It is expected as a result that only those DNA mixtures which contain methylated bisulfite-converted DNA produce positive signals. The signals should be independent of the quantity of original unmethylated background DNA (see: Table 1).

Example 3

"Increase of the Sensitivity of a 'HeavyMethyl' Assay by Use of the Heat-Stable TDG Protein from *Methanobacterium thermoautotrophicum* THF"

The DNA sequence (Seq-ID 1, Seq-ID 2, Seq-ID 8) described in Example 1 is amplified by means of PCR. The bisulfite-converted human DNA from the same source also described therein is used as the template DNA. A methylation-specific blocker oligonucleotide (Seq-ID 7) is additionally contained in the PCR batch. In this way, a methylation-specific amplification is obtained (see above). The sequence of the blocker is selected in such a way that it spans 3 CpGs and is complementary to unmethylated bisulfite-converted DNA. In contrast to the conventional "HeavyMethyl" assay, one nucleotide was exchanged in the blocker at position 10. Instead of adenosine, guanosine was incorporated, which forms G<->T erroneous pairings in the hybridization of the blocker to the bisulfite-converted DNA. The heat-stable TDG protein, which recognizes G<->T erroneous pairings and removes the thymine base from the DNA so that abasic regions are formed, is also contained in the PCR batch. A pre-incubation of the PCR batch in the case of a blocker-specific hybridization temperature thus leads to the specific degradation of unmethylated bisulfite-converted template DNA. A degradation of methylated DNA is prevented in this way, so that the hybridization of the blocker occurs in a methylation-specific manner. During the PCR, the blocker also functions as a blocker oligonucleotide. Since the heat-stable TDG protein remains active, however, unmethylated DNA is additionally degraded in each additional PCR cycle. In contrast to the conventional "HeavyMethyl" assay, thus the amplification of unmethylated DNA is prevented by a blocker oligonucleotide, but in addition, unmethylated bisulfite-converted DNA is degraded. By combining the "HeavyMethyl" technology with the specific decomposition of erroneous pairing by the TDG protein, a substantial increase in the relative sensitivity is achieved.

The temperature program contains two additional incubation cycles at 56° C., in order to reduce the fraction of unmethylated DNA even prior to the beginning of the PCR. The reaction batch is conducted into capillaries provided for it in the LightCycler-1.3 system.

The following are contained in 20 µl of reaction volume (sequences in Table 2): 10 µl of template DNA; 2 µl of FastStart LightCycler Mix for hybridization probes (Roche Diagnostics); 2.0 mmol/l MgCl$_2$ (Roche Diagnostics); 0.30 µmol/l forward primer (Seq ID-1, TIB-MolBiol); 0.30 µmol/l reverse primer (Seq ID-2, TIB-MolBiol); 0.15 µmol/l probe 1 (Seq ID-3, TIB-MolBiol); 0.15 µmol/l probe 2 (Seq ID-4, TIB-MolBiol); 1 unit of heat-stable TDG glycosylase (Trevigen); 1 µmol/l blocker oligonucleotide (Seq ID-7, TIB MolBiol).

The following temperature program is utilized: 2 temperature cycles: 10 sec at 95° C.; 5 min at 56° C.; activation of the polymerase: 10 min at 95° C.; 55 temperature cycles: 10 sec at 95° C.; 10 sec at 56° C.; 10 sec at 72° C. Then the reaction is cooled to 35° C.

The fluorescent signals are measured in channel F2. The evaluation of the PCR is conducted automatically by means of the LightCycler software in mode F2/F1. Signals which lie significantly above the background signal of the negative controls are considered positive. It is expected as a result that only those DNA mixtures which contain methylated bisulfite-converted DNA produce positive signals. The signals should be independent of the quantity of original unmethylated background DNA (Table 1).

TABLE 1

Expected results with different DNA mixtures.

| Sample no. | ng of methylated DNA in 10 µl of DNA mixture | ng of unmethylated DNA in 10 µl of DNA mixture | Expected result |
|---|---|---|---|
| 1 | 1.0 | 0.0 | positive |
| 2 | 1.0 | 1.0 | positive |
| 3 | 1.0 | 10.0 | positive |
| 4 | 1.0 | 100.0 | positive |
| 5 | 0.1 | 0.0 | positive |
| 6 | 0.1 | 1.0 | positive |
| 7 | 0.1 | 10.0 | positive |
| 8 | 0.1 | 100.0 | positive |
| 9 | 0.0 | 0.0 | negative |
| 10 | 0.0 | 1.0 | negative |
| 11 | 0.0 | 10.0 | negative |
| 12 | 0.0 | 100.0 | negative |

TABLE 2

Sequences of oligonucleotides

| Seq-ID | Name | Sequence |
|---|---|---|
| Seq-ID-1 | brac1-F1 | 5'-GAAGtTGAtAGATGGGTATTtTTTGA |
| Seq-ID-2 | brac1-R1 | 5'-CCCCCTTCCTaATCCTCAa |
| Seq-ID-3 | brca1-fluo | 5'-GCGGAAttTGAGAGGCGTA-fluo |
| Seq-ID-4 | brac1-red | 5'-red640-GCGTTGTGAAtttTGGGGAG-pho |
| Seq-ID-5 | Mismatch probe 1 | 5'-CACAACGCCTTACGCCTCTC-pho |
| Seq-ID-6 | Mismatch probe 2 | 5'-CAAATTCCGCCCCTACCCCCC-pho |
| Seq-ID-7 | Mismatch blocker | 5'-TAATCCTCAGCACTTCCCTCACAACCT-pho |
| Seq-ID-8 | brca1-amplicon | 5'GAAGtTGAtAGATGGGTATTtTTTGACGGGGGGTAGGGGCGGAAttTGAGAGGCGTAAGGCGTTGTGAAtttTGGGGAGGGGGGtAGTTTGTAGGTCGCGAGGGAAGCGtTGAGGATtAGGAAGGGGG | fluo = 3'-fluorescein modification (TIB-MolBiol),
red640 = 5'-fluorescein modification for channel F2 (TIB MolBiol),
pho = 3'-phosphate modification (TIB-MolBiol)
Unmethylated cytosines converted by bisulfite conversion are shown as "t" in the sequence.
Unconverted methylated cytosines remain as "C" in CpGs.

The invention claimed is:

1. A method for the analysis of methylated DNA as compared to background DNA of the same sequence but another methylation pattern comprising:
   a) converting the DNA to be investigated chemically or enzymatically so that 5-methylcytonise remains unchanged, while unmethylated cytosine is converted to uracil or to another base which differs from cytosine in its base pairing behavior,
   b) hybridizing the converted DNA with oligonucleotides, whereby the background DNA forms hybrids with erroneous base pairings,
   c) cleaving the converted DNA strand of the erroneously paired hybrids enzymatically,
   d) amplifying the uncleaved converted DNA,
   e) detecting the amplificates,
   f) concluding the methylation status of the investigated DNA from the detection signal generated in step e),
   g) wherein steps b) through d) are conducted simultaneously.

2. The method according to claim 1, wherein the background DNA forms several erroneous base pairings with the oligonucleotides.

3. The method according to claim 1, wherein the oligonucleotides utilized in step b) are simultaneously utilized as primers or probes in an amplification step.

4. The method according to claim 1, wherein the amplification or the detection of the amplificates is carried out in a methylation-specific manner.

5. The method according to claim 1, wherein said amplifying step comprises amplifying several fragments simultaneously.

6. The method according to claim 1, wherein the detection in step e) is made by means of a microarray.

7. The method according to claim 1, wherein said cleaving step of step c) comprises utilizing a DNA repair enzyme.

8. The method according to claim 7, wherein said DNA repair enzyme is selected from the group consisting of MutY, Mug protein, DNA glycosylase and TDG enzyme.

9. The method according to claim 7, wherein said DNA repair enzyme is heat-stable.

10. The method according to claim 8, wherein the TDG enzyme is heat-stable.

11. The method for the diagnosis or prognosis of cancer disorders or other diseases associated with a change in the cytosine methylation status, for predicting undesired drug interactions, for establishing a specific drug therapy, for monitoring the success of a drug therapy, for distinguishing cell types or tissues and for investigating cell differentiation, said method comprising analysis of methylated DNA as compared to background DNA of the same sequence but another methylation pattern, and further comprising the steps of:
   a) converting the DNA to be investigated chemically or enzymatically so that 5-methylcytonsine remains unchanged, while unmethylated cytosine is converted to uracil or to another base which differs from cytosine in its pairing behavior,
   b) hybridizing the converted DNA with oligonucleotides, whereby the background DNA forms hybrids with erroneous base pairings,
   c) cleaving the converted DNA strand of the erroneously paired hybrids enzymatically,
   d) amplifying the uncleaved converted DNA,
   e) detecting the amplificates,
   f) using the detection signal generated in step e) to obtain a diagnosis or prognosis of cancer disorders or other diseases associated with a change in the cytosine methylation status, to predict undesired interactions, to establish a specific drug therapy, to monitor the success of a drug therapy, to distinguish cell types or tissues and to investigate cell differentiation,
   g) wherein steps b) through d) are conducted simultaneously.

12. The method for the early diagnosis of cancer disorders or other diseases associated with a change in the cytosine methylation status, said method comprising analysis of methylated DNA as compared to background DNA of the same sequence but another methylation pattern, and further comprising the steps of:
   a) converting the DNA to be investigated chemically or enzymatically so that 5-methylcytonsine remains unchanged, while unmethylated cytosine is converted to uracil or to another base which differs from cytosine in its pairing behavior,
   b) hybridizing the converted DNA with oligonucleotides, whereby the background DNA forms hybrids with erroneous base pairings,
   c) cleaving the converted DNA strand of the erroneously paired hybrids enzymatically,
   d) amplifying the uncleaved converted DNA,
   e) detecting the amplificates,
   f) using the detection signal generated in step e) for the early diagnosis of cancer disorders or other diseases associated with a change in the cytosine methylation status,
   g) wherein steps b) through d) are conducted simultaneously.

13. The method according to claim 1 further comprising the step of isolating the DNA to be investigated from a body fluid sample of an individual.

14. The method according to claim 1 further comprising the step of isolating the DNA to be investigated has been isolated from a serum, plasma, sperm, urine or stool sample of an individual.

* * * * *

SEQUENCE LISTING

<160> NUMBER OF SEQ ID NOS: 8

<210> SEQ ID NO 1
<211> LENGTH: 26
<212> TYPE: DNA
<213> ORGANISM: Artificial Sequence
<220> FEATURE:
<223> OTHER INFORMATION: chemically treated genomic DNA (Homo sapiens)

<400> SEQUENCE: 1
gaagttgata gatgggtatt ttttga                26

<210> SEQ ID NO 2
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 2
ccccctccct aatcctcaa                                                19

<210> SEQ ID NO 3
<211> LENGTH: 19
<212> TYPE: DNA
<213> ORGANISM: Artificial Sequence
<220> FEATURE:
<223> OTHER INFORMATION: chemically treated genomic DNA (Homo sapiens)

<400> SEQUENCE: 3
gcggaatttg agaggcgta                                                19

<210> SEQ ID NO 4
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 4
gcgttgtgaa ttttggggag                                               20

<210> SEQ ID NO 5
<211> LENGTH: 20
<212> TYPE: DNA
<213> ORGANISM: Artificial Sequence
<220> FEATURE:
<223> OTHER INFORMATION: chemically treated genomic DNA (Homo sapiens)

<400> SEQUENCE: 5
cacaacgcct tacgcctctc                                               20

<210> SEQ ID NO 6
<211> LENGTH: 21
<212> TYPE: DNA
<213> ORGANISM: Artificial Sequence
<220> FEATURE:
<223> OTHER INFORMATION: chemically treated genomic DNA (Homo sapiens)

<400> SEQUENCE: 6
caaattccgc ccctaccccc c                                             21

<210> SEQ ID NO 7
<211> LENGTH: 27
<212> TYPE: DNA
<213> ORGANISM: Artificial Sequence
<220> FEATURE:
<223> OTHER INFORMATION: chemically treated genomic DNA (Homo sapiens)

<400> SEQUENCE: 7
taatcctcag cacttccctc acaacct                                       27

<210> SEQ ID NO 8
<211> LENGTH: 128
<212> TYPE: DNA
<213> ORGANISM: Artificial Sequence
<220> FEATURE:

```
<223> OTHER INFORMATION: chemically treated genomic DNA (Homo sapiens)

<400> SEQUENCE: 8
gaagttgata gatgggtatt ttttgacggg gggtaggggc ggaatttgag aggcgtaagg        60
cgttgtgaat tttggggagg ggggtagttt gtaggtcgcg agggaagcgt tgaggattag       120
gaaggggg                                                                128
```